(12) United States Patent
Scott

(10) Patent No.: US 7,334,450 B1
(45) Date of Patent: Feb. 26, 2008

(54) WATER CUT MEASUREMENT WITH IMPROVED CORRECTION FOR DENSITY

(75) Inventor: Bentley N. Scott, Garland, TX (US)

(73) Assignee: Phase Dynamics, Inc., Richardson, TX (US)

(*) Notice: Subject to any disclaimer, the term of this patent is extended or adjusted under 35 U.S.C. 154(b) by 311 days.

(21) Appl. No.: 11/273,613

(22) Filed: Nov. 14, 2005

Related U.S. Application Data

(60) Provisional application No. 60/627,436, filed on Nov. 12, 2004.

(51) Int. Cl.
*G12B 13/00* (2006.01)
*G01C 25/00* (2006.01)

(52) U.S. Cl. .............. 73/1.02; 73/32 R; 73/61.44; 702/25; 702/137; 702/104

(58) Field of Classification Search ............... 73/1.01, 73/1.02, 1.88, 32 R, 53.01, 61.41–61.49; 702/23, 25, 137, 100, 104
See application file for complete search history.

(56) References Cited

U.S. PATENT DOCUMENTS

| | | | |
|---|---|---|---|
| 3,693,435 A * | 9/1972 | Cox et al. ............... 73/861.04 |
| 4,947,127 A * | 8/1990 | Helms et al. ............... 324/640 |
| 5,259,239 A | 11/1993 | Gaisford |
| 5,260,667 A | 11/1993 | Garcia-Golding et al. |
| 5,576,974 A | 11/1996 | Marrelli et al. |
| 5,654,502 A | 8/1997 | Dutton |
| 6,234,030 B1 | 5/2001 | Butler |
| 6,318,156 B1 | 11/2001 | Dutton et al. |
| 6,327,914 B1 | 12/2001 | Dutton |
| 6,931,342 B2 * | 8/2005 | Mann et al. ............... 702/105 |
| 2005/0081643 A1 | 4/2005 | Mattar et al. |

FOREIGN PATENT DOCUMENTS

| | | |
|---|---|---|
| EP | 870196 B1 * | 3/2000 |
| GB | 2376074 A * | 12/2002 |
| WO | WO 2005109012 A1 * | 11/2005 |

* cited by examiner

*Primary Examiner*—Helen Kwok
*Assistant Examiner*—David A. Rogers

(57) ABSTRACT

Methods of correcting on-line analyzer measurements of the content of a first component, e.g., water, in a multiple-component fluid, e.g., petroleum, are provided. The first component content measurements in a flowing multiple-component fluid may be taken using an on-line analyzer. Mixture density measurements that correspond to the first component content measurements may also be taken using a densitometer. Next, an offset value for each first component content measurement may be calculated based on the following equations:

if the first component content measurement is ≦ a predetermined content set point, offset=slope correction factor×(the corresponding mixture density measurement−a calibration density); and    (a)

if the first component content measurement is > the predetermined content set point, offset=the offset value calculated at the predetermined content set point.    (b)

The first component content measurements may then be corrected based on the respective offset values.

20 Claims, 9 Drawing Sheets

WATER CUT MEASUREMENT WITH IMPROVED CORRECTION FOR DENSITY

CROSS-REFERENCE TO RELATED APPLICATIONS

This application claims priority from U.S. provisional patent application 60/627,436 filed on Nov. 12, 2004, which is hereby incorporated by reference.

BACKGROUND AND SUMMARY OF THE INVENTION

The present application relates generally to systems and methods for analysis of produced petroleum, and more particularly to correcting on-line permittivity based analyzer measurements of water content in petroleum.

The following paragraphs contain some discussion, which is illuminated by the innovations disclosed in this application, and any discussion of actual or proposed or possible approaches in this Background section does not imply that those approaches are prior art.

Measurement of the quantity, density, average temperature, and water percentage in petroleum has been an important issue to the petroleum industry. The methods of measurement have been investigated and have undergone continued improvement over the years. Composite samplers are commonly used as the standard by which water content is determined in petroleum as it is being transported in pipelines. A composite sampler is a system that obtains a small sample from a pipeline proportional to time or volume to represent the entire petroleum load. Unfortunately, results for composite samplers are typically only available at the end of a batch, and there is no recourse if something goes wrong with the sampling system during the batch. At the end of the batch only a single number is available to consider. Originally petroleum products contained only a narrow range of densities, and due to this fact composite samplers required testing against one density of oil. Today petroleum products contain a much larger variation in types of crude oils and densities. However, composite samplers are typically validated on one type of product with the assumption that they are valid for all densities and types. Moreover, the exposure of personnel to hazardous liquids and the errors associated with processing the samples are additional concerns with using composite samplers.

Accordingly, the use of on-line real time analyzers such as capacitance, RF (i.e., radio frequency), and microwave analyzers to measure the water content of petroleum products is becoming more common. Real time data can provide several beneficial operational advantages. Knowledge of when water becomes present in petroleum as it is being produced and the magnitude of the water may provide an opportunity to remove the water before it reaches transport via pipeline or shipping tank. The real time data may show if the water is detected in several short periods of time or if it is present across the entire load of the petroleum. In addition, real time analyzers may be used as a comparison of the validity of the composite samplers.

Unfortunately, measurements such as those described above are usually subject to an uncertainty value, which is typically expressed as a standard deviation from a mean value. Knowing the uncertainty value ensures that informed decisions can be made about the data collected. An on-line water content analyzer relies on representative samples of the actual flowing stream just like a composite sampler probe. As such, the measurements of the on-line analyzer are only as good as the representative samples taken and thus may be affected by many influences. For example, the analyzer readings may be subject to random uncertainty sources such as changes in the ambient temperature. Moreover, they may also be subject to systematic uncertainty sources such as improper analyzer calibration, improper correction of the liquid temperature which can experience variations, insufficient mixing of the petroleum product due to, e.g., low flow rate, water content above the range of detection, and variations in the properties of the different crude oils present such as viscosity, emulsion, and density.

Capacitance, RF, and microwave on-line water content analyzers are particularly affected by the "wet" oil density and "dry" oil density of the petroleum. The "wet" oil density is the measured density of the oil and the water in the petroleum, whereas the "dry" oil density is the measured density of only the oil in the petroleum. The basis of the effect of the wet and dry oil densities is that such on-line analyzers detect changes in the polar moment of a molecule, which affects the electrical properties of permittivity and thus the dielectric constant, i.e., the normalized real part of permittivity. Those on-line analyzers are more sensitive to the water molecule because the parameter of measurement is the large difference between the small polar moment of crude oils (dielectric constant ranges from 2 to 2.5) and the high polar moment of water (dielectric constant ranges from 68-80).

The density of a petroleum product is therefore relational to the dielectric constant. This relationship is illustrated in FIG. 9, which shows that the dielectric constant decreases as the wet oil density of the petroleum, i.e., the American Petroleum Institute (API) gravity, increases. The dielectric constant also decreases as the dry oil density of the petroleum increases. It is therefore desirable to develop methods for correcting the on-line water content analyzer measurements for wet and dry oil densities.

Water Cut Measurement with Improved Correction for Density

The present application describes systems and methods for measuring the water fraction ("water cut") in a stream of crude oil. A measurement of physical density is used to supply a correction factor for the electrical on-line characterization of water cut, but the correction factor is capped to that for a modest water fraction, e.g. 5%. This ensures that corrected measurements are achieved at low densities as before, while avoiding error due to overcorrection at higher water fractions.

The disclosed innovations, in various embodiments, provide one or more of at least the following advantages:

More accurate measurements at high water cuts;
Accurate measurements at low water cuts;
Simple implementation.

BRIEF DESCRIPTION OF THE DRAWING

The disclosed inventions will be described with reference to the accompanying drawings, which show important sample embodiments of the invention and which are incorporated in the specification hereof by reference, wherein.

DETAILED DESCRIPTION OF THE PREFERRED EMBODIMENTS

Figure 1:
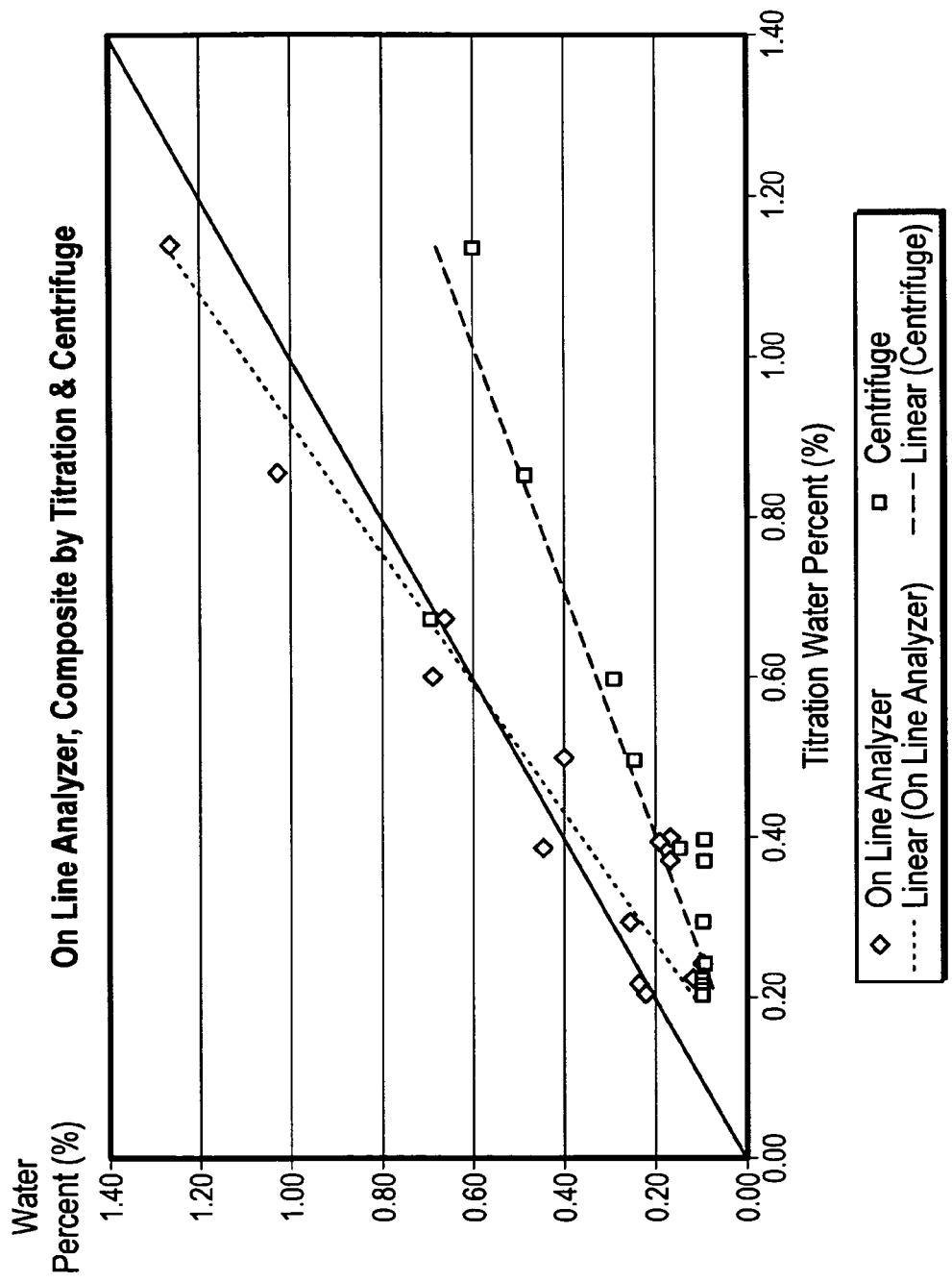
FIG. 1 shows a comparison of data achieved by titration, centrifugation, and a real time water analyzer.

The numerous innovative teachings of the present application will be described with particular reference to the presently preferred embodiment (by way of example, and not of limitation).

Some teachings and advantages found in the present application are summarized briefly below. However, note that the present application may disclose multiple embodiments, and not all of the statements in this section necessarily relate to all of those embodiments. Moreover, none of these statements limit the claims in any way.

Measurement of the quantity, density, average temperature and water percentage in petroleum pipelines has been an issue of prime importance. The methods of measurement have been investigated and have seen continued improvement over the years. Questions are being asked as to the reliability of the measurement of water in the oil through sampling systems originally designed and tested for a narrow range of densities. Today most facilities sampling systems handle vastly increased ranges of density and types of crude oils. Issues of pipeline integrity, product loss and production balances are placing further demands on the issues of accurate measurement. Water percentage is one area that has not received the attention necessary to understand the many factors involved in making a reliable measurement.

A previous paper (Scott, "Uncertainties in Pipeline Measurement," in *Proceedings of IPC 2004 International Pipeline Conference*, Calgary, Alberta, Canada. IPC04-0046, Oct. 4-8, 2004) discussed the issues of uncertainty of the measurement from a statistical perspective. This paper will outline many of the issues of where the errors lie in the manual and automatic methods in use today. A routine to use the data collected by the analyzers in the on line system for validation of the measurements will be described.

Composite samplers have been used as the standard by which water content is determined in pipelines. Losses and gains between tankage and pipeline, marine unloading and shore may reflect an acceptable mean value but is the system within acceptable control limits? Results for composite samplers are only available at the end of a batch and there is no recourse if something goes wrong with the sampling system during the batch. At the end of the batch only a single number is available to argue about the water delivered. The exposure of personnel to hazardous liquids and the errors associated with processing the samples are additional issues. On line real time analysis of the water content can be obtained with analyzers on the market today. Real time data makes it possible to know when the water arrived providing several beneficial operational advantages. Knowledge of when the water arrives and the magnitude provides an opportunity to do something with the water before it hits the pipeline or tankage. The real time data can show if the water was several short periods of time or if it was across the entire load. In addition, real time analyzers can be used as a comparison of the validity of the composite samplers, something not done until recently.

Originally pipelines only shipped products with a narrow range of densities and due to this fact composite samplers only required testing against one density of oil. Today pipelines ship products with extremely large variation in density and molecular chemistry but the older methods of validation are still in place using one or two densities. Samplers are typically proved on one type of product with the assumption that it is valid for all densities and types. Original API methods suggested testing on the lightest density oil. If the oil becomes heavy, cold and very viscous does the sampler provide the same acceptable deviation from acceptance tests? There are many more issues and questions which must be asked to determine the overall system performance.

The better a process can be understood and the errors controlled the easier it is to assure a good measurement. Each process will be analyzed for the potential errors and their sources. Finally, a new analysis routine will be investigated to compare the on line measurements.

1—UNCERTAINTY

The petroleum industry generates and uses volumes of data used to buy, sell and balance production. Unfortunately, the documentation with this data typically does not contain statements of uncertainty. Decisions about expectations and corrective actions cannot be made without a statement of uncertainty typically expressed as a standard deviation from a mean value. The standard deviation can only be obtained through taking enough data that can then be used to generate the statistical comparisons against some other method. If there is no other standard to compare against then the uncertainty cannot be obtained. There have been statements about loading losses by crude types and losses for load and receipt terminals but are these statements qualified for all of the contributing factors?

If one composite sample is obtained and laboratory methods performed with two different analysis techniques, what does the uncertainty analysis represent? The composite sample container, Sample 1, is mixed then a sample pulled that is Sample 2. Now the laboratory takes this Sample 2 and pulls two more samples one for titration, Sample 3, and another for distillation Sample 4. This results in a statistical analysis determining the uncertainty between the two laboratory methods and the ability to pull the Samples 3 & 4 from Sample 2. Therefore, if the sample itself is processed using two independent laboratory methods this routine will only check the uncertainties of the two laboratory methods and the operator's ability to pull a sample from the larger composite sample. Nothing can be said about the uncertainty of the actual in line measurement because the sample into the composite sampler has nothing for comparison.

If API Chapter 8.2 is followed to prove the composite system, the allowable deviation for 1% level of water in a batch is 0.11% and for under 0.5% water the allowable is 0.09%. These numbers are relational to the testing of the composite system by water injection. If the system has been tested on several crude types it is likely that they do not represent the entire spectrum of crude types being shipped through the system after the testing was completed. Therefore, the results may or may not fall in the allowable deviation seen during the injection water testing. Therefore the remaining question is how can the measurement be validated not only across crude types but also for every batch shipped?

Can anything be said about accuracy of the measurement? Accuracy must be compared against a known standard.

There does not exist a standard by which to measure the water in the crude oil that is flowing with a specific chemical structure, density, temperature, pressure, viscosity and water content equal to what is in the line. The best that can be done is to qualify a system against an independent measurement for the validity of measurement uncertainty, not accuracy. Independent means that it is not dependent upon the same sample or method of measurement.

If an on line analyzer is installed in a separate fast loop or in line then this is independent of the sampling mechanics of the composite system. This analyzer can be used to aid in arriving at the uncertainty of the measurement when using the composite system. The analyzer should be located in a position that is viewing the main liquid stream in the same homogeneous state as the mechanical sampler. If both methods are reproducible then the resulting uncertainty analysis will be meaningful and one can be used to aid in validation of the other.

2—DISCUSSION OF DATA FOR A PIPELINE

The following data in Table 1 was collected by the operators and entered manually into a worksheet and is representative of many types of data collection in the field. The unusual aspect of this table was that it contains several laboratory methods (Karl Fisher and centrifuge) instead of the usual one lab method and the density was quite consistent through the entire month of data.

Another aspect of this data is seen when the trend lines are compared with the least error line that is a 45 degree line between the two graph end points. The centrifuge versus the titration is showing the centrifuge consistently low while the comparison with the on line analyzer shows titration slightly less in water than expected. Normally centrifuge is expected to produce a lower water percentage than titration. Since all of the data consisted of moderate crude density and viscosity the centrifuge results would have been expected to be closer to the same water result as the titration.

3—SHIP UNLOADING DATA

The following examples were from an on line analyzer and a composite sampler using titration as the laboratory method. All of the data collection was by computer with checks for the composite sampler built into the data collection.

Figure 2:
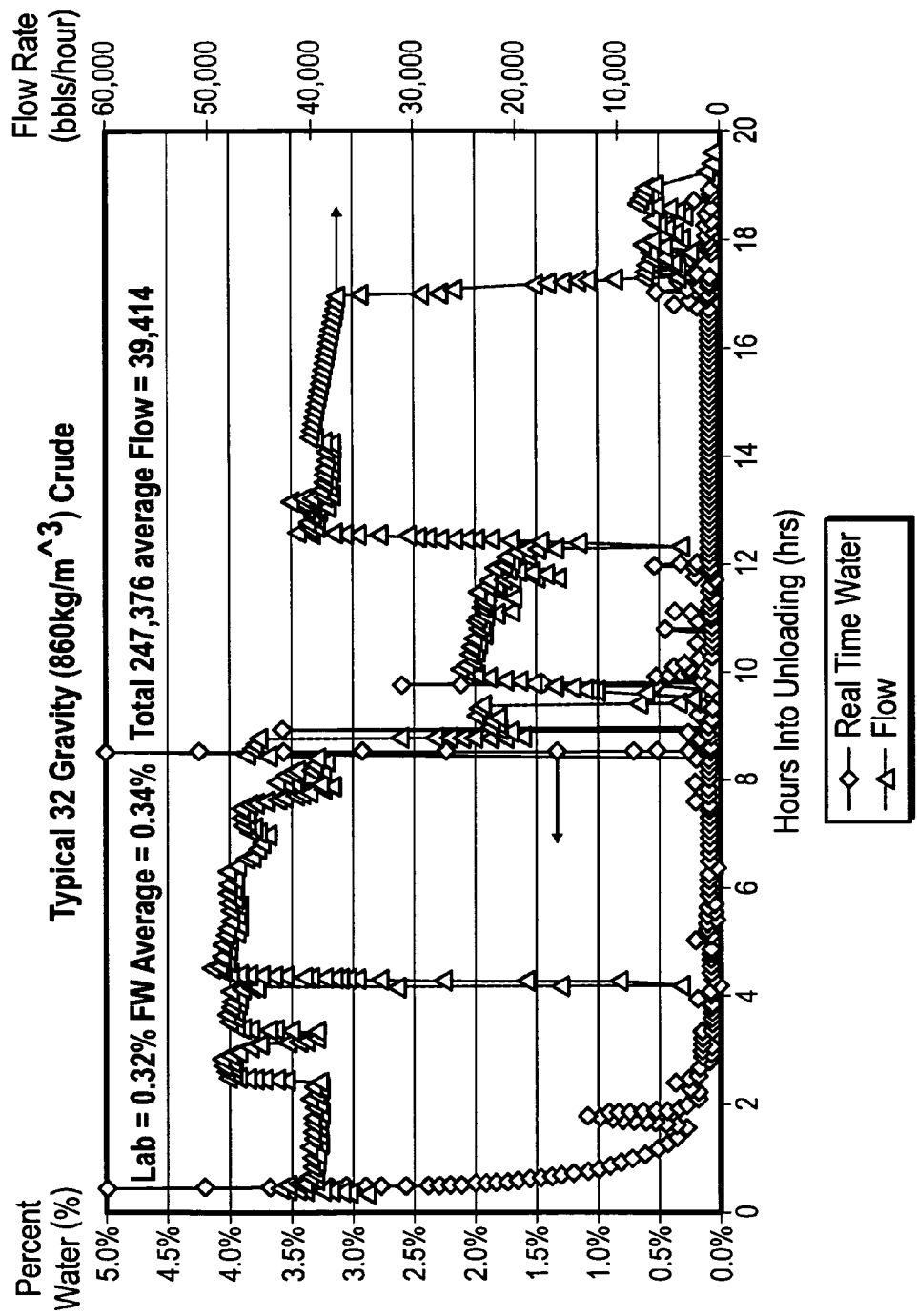
FIGS. 2 and 3 show sample ship unloading profiles.

In the ship unloading profile of FIG. 2 the flow started and stopped, ran at one half the rate for several hours and had some very large water spikes. The results from the composite sampler were 0.32% water using titration and the flow weighted average from the on line water analyzer gave 0.34%. Very good results with the lab compared to the on line analyzer with the standard density crude oil. What happens when the same facility receives a higher density and viscous oil?

TABLE 1

Hand Entered Batch Data

| Date | Batch # | Analyzer % Water | KF % Water | Grind Out % Water | Avg.Batch Density | API at 60 | Obs.Grav. | Obs.Temp | (BBLs) |
|---|---|---|---|---|---|---|---|---|---|
| Apr. 1, 2003 | 52 | 0.17 | 0.40 | 0.20 | 0.8575 | 32.2 | 33.3 | 75 | 197931 |
| Apr. 4, 2003 | 55 | 1.27 | 1.14 | 0.60 | 0.8567 | 32.1 | 32.0 | 58 | 115454 |
| Apr. 6, 2003 | 56 | 0.45 | 0.39 | 0.15 | 0.8559 | 32.2 | 32.1 | 58 | 78690 |
| Apr. 9, 2003 | 57 | 0.17 | 0.37 | 0.10 | 0.8548 | 32.4 | 33.3 | 72 | 196547 |
| Apr. 10, 2003 | 58 | 0.10 | 0.24 | 0.10 | 0.8571 | 32.1 | 33.0 | 72 | 78624 |
| Apr. 12, 2003 | 59 | 0.12 | 0.23 | 0.10 | 0.8564 | 32.1 | 33.1 | 74 | 182087 |
| Apr. 14, 2003 | 60 | 0.24 | 0.22 | 0.10 | 0.8552 | 32.0 | 33.0 | 74 | 78626 |
| Apr. 16, 2003 | 61 | 0.23 | 0.21 | 0.10 | 0.8538 | 32.2 | 33.2 | 73 | 197371 |
| Apr. 17, 2003 | 62 | 0.26 | 0.30 | 0.10 | 0.8565 | 31.7 | 33.0 | 78 | 78733 |
| Apr. 20, 2003 | 63 | 0.40 | 0.40 | 0.10 | 0.8500 | 33.0 | 33.2 | 63 | 183877 |
| Apr. 23, 2003 | 65 | 1.03 | 0.85 | 0.50 | 0.8507 | 32.8 | 32.9 | 62 | 78546 |
| Apr. 25, 2003 | 66 | 0.67 | 0.67 | 0.70 | 0.8548 | 31.7 | 33.4 | 83 | 65583 |
| Apr. 27, 2003 | 67 | 0.69 | 0.60 | 0.30 | 0.8541 | 32.1 | 33.6 | 80 | 130832 |
| Apr. 29, 2003 | 68 | 0.40 | 0.50 | 0.25 | 0.8548 | 31.9 | 33.4 | 80 | 120000 |
| | | | | | | | | | 1782901 |

The data is from a composite sampler on a pipeline across a month where all of the data was obtained with one operator using a laboratory that followed API standards closely. The real time water analyzer was installed after the static mixer and sampling system. The results are shown in FIG. 1. The dotted lines represent the best-fit line through the data. In this case the on line analyzer compared favorably with the composite by titration but composite by centrifuge shows the water much lower. More data may change the analyzer trend line to fall more correctly without a skewed slope against the titration. Another question this trend may ask is if the titration is biased at higher water percentages. One centrifuge point (batch 66) which appeared to be a bad data point was correct with respect to titration. Possibly this was an error in the entry of the centrifuge result or some operator influence, as it would be expected to follow the same trend as the other centrifuge points.

Figure 3:
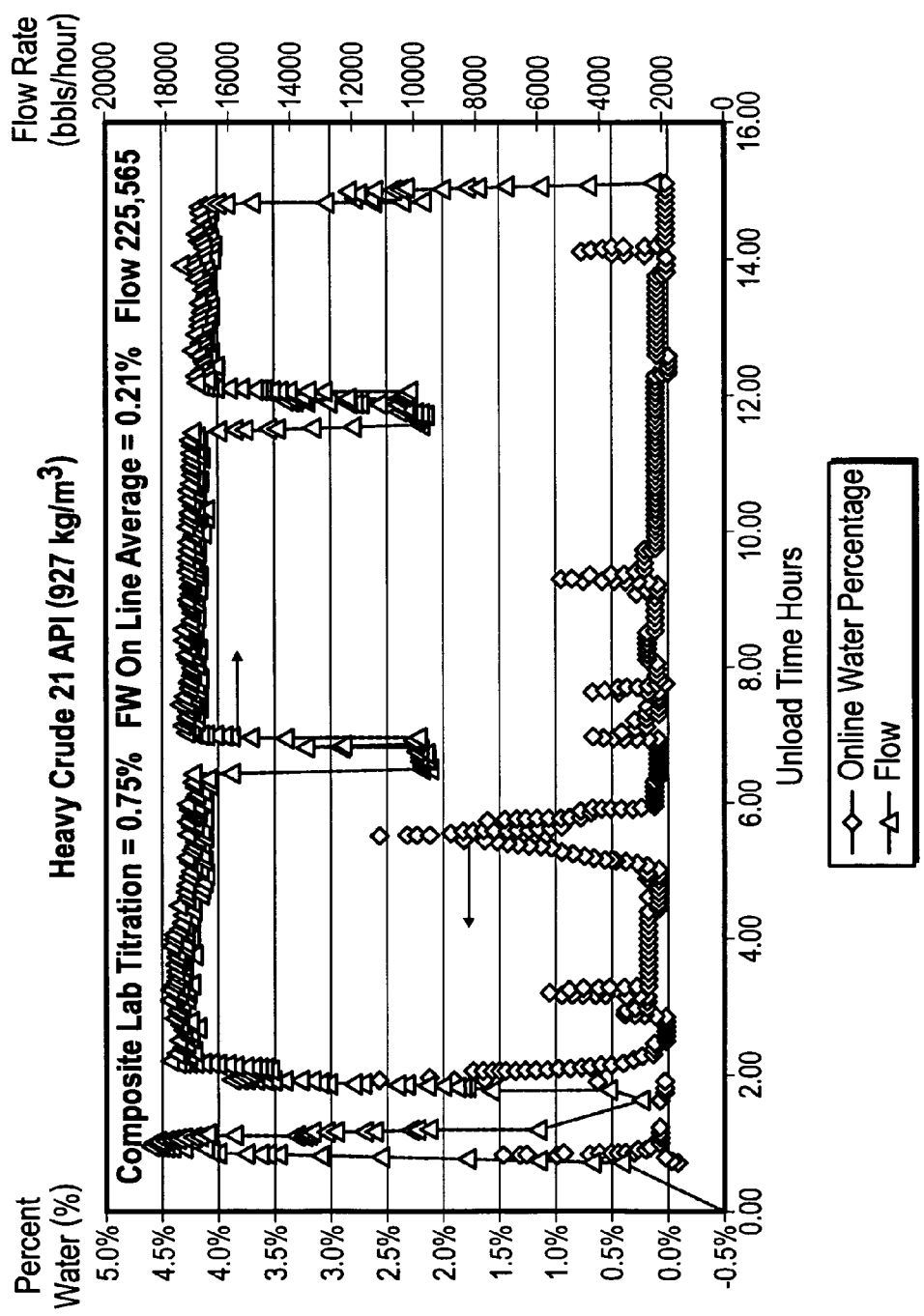

FIG. 3 is a graph for a ship unloading profile for a 21 degree API density crude oil. Now the laboratory results from the composite sampler are much higher than the on line analyzer. Which one is correct? This question would not be asked without the on line analyzer for comparison. The composite sampler was not tested against this heavy crude.

The measurement of density affects the offset calculated for the on line water analyzer baseline and defines where zero water percentage is with respect to density. Was it simply an offset calculation problem or a density measurement issue? Did the sampler have trouble with the higher viscosity of this crude oil? Was there bias in handling the heavy, cold crude oil in the laboratory? Was there a chemical interference with the titration from some component in the crude oil? Although the chemical interference was suspected and partially proven, no answers to these questions were acceptable with enough certainty to be accepted as true. The composite sampler was correct because it was the standard.

4—UNCERTAINTY COMPONENTS

In the petroleum industry the measurement of water cut using centrifuge could have the following uncertainty components (not all inclusive): sample probe location in the main pipeline (center ⅓, wall, top, bottom), sample probe size, valve type and size, upstream conditioning (mixer, elbow, two elbows), flow rate in main line, flow rate in sample probe, difference in pressure between line and atmosphere, temperature differences between ambient and liquid, sample container material, size and type of seal for lid, volume of sample, time before processing sample, mixing of sample before extraction to centrifuge tube, solvent type used, de-emulsifier type, temperature of centrifuge, oil type and viscosity, type of centrifuge tube, operator reading the meniscus, solids content, and clarity of the water.

Table 2 is a partial description of what may define systematic and random uncertainties. These components of the total uncertainty need to be separated and discussed as to the contributions in each portion of the measurement. The British Standard Methods for Sampling Petroleum Products, Part 2 (BS3195: Part 2:1989, IS)3171:1988) defines the formula for uncertainty calculations where the Relative Systematic Uncertainties are additive while the Relative Random Uncertainties are relational to one fourth of the sum of the squares of the relative random uncertainties. Relative uncertainty is the uncertainty of a factor divided by the value of the factor.

TABLE 2

How to Recognize Systematic and Random Uncertainty

| Systematic Uncertainty | Random Uncertainty |
| --- | --- |
| Also Known As Resolution, Bias Reproducible Inaccuracy Produced by Technique, Improper Calibration, Faulty Equipment | Variable Must be Defined and Eliminated to Reduce Errors More Data Does Not Help Because The Effect is Random People Make Random Mistakes |
| More Data Points Can Define Uncertainty Easier To Find and Solve Than Random Effects People Making Systematic Mistakes | Skip A Known Step Once Transpose Numbers Only the Probability of an Error Occurring Can Be Discussed |
| Doing The Wrong Thing Consistently Missing a Step in the Process All The Time | |

As defined by the British Standard, there are two numbers for each line below, one for the systematic and one for the random uncertainty:
non-homogeneity of the water content;
changes in the water content caused by sampling;
uncertainty of the grab volume;
uncertainty in the flow rate causing non-proportionality of sampling;
changes in the water content during sampling;
changes in the water content caused by sample handling and mixing;
changes in the water content caused by transfer to laboratory apparatus.

The systematic uncertainties add, and therefore they are the most important source of errors.

5—SOURCES OF UNCERTAINTY FOR A COMPOSITE SAMPLER

Table 3 suggests some of the uncertainty components for the composite sampler. Notice that many of these are related to people handling and inspecting the process. Although many can be automated for verification that the process is progressing during a batch sample, all cannot be controlled simply by monitoring. In the British Standard, description of the variables number one through four describe the expected issues with the sampler.

TABLE 3

Systematic and Random Components for Sampler System

| Systematic Uncertainty | Random Uncertainty |
| --- | --- |
| "Line Fill" Issues | Improper Entry of Batch Size |
| Emulsion Size Vs Probe Size Flow or Timed Proportional Oil Density - Light or Heavy Mixing of Main Crude Stream Sampling Probe Method/Condition Sample Container | Gives Small Sample Size Overfills Container Sample Container Cleaning Sample Container Change Out Didn't Occur Ambient Temperature Variations |
| Level of Fill Switching for Large Batch | Sun, Rain, Hot/Cold People Oriented Random Errors |
| Cleanliness Temperature Effects on Sampling Operator Change Composite Sample To Lab Sample Mixing & Extraction | Recording Data Handling/Setting System Shift Change During Batch End |

6—SOURCES OF UNCERTAINTY FOR A LABORATORY ANALYSIS

Table 4 suggests some of the uncertainties that may be found in the laboratory. In these steps the personnel become one of the most important influences to uncertainty. In the British Standard, description of the variables number five through seven describe the expected issues with the laboratory.

TABLE 4

Table for Laboratory Uncertainty

| Systematic Uncertainty | Random Uncertainty |
| --- | --- |
| Obtaining Sample of Composite Sample For Analysis Density/Viscosity Effects Proper Preparation of Apparatus and Chemicals Measuring Volumes Properly | Length of Time Before Analysis Performed After Sample Obtained Temperature of Sample Shift Changes During Analysis Personnel Dependent Variables Random Types |
| Reading Meniscus Personnel Dependent Variables Not Random | Optical Readings Variance Caused by Colds, Allergies Night vs Day Awareness |
| Methodology Diligence | Improper Recording of Numbers |

7—DENSITY MEASUREMENT UNCERTAINTIES

The typical online measurement of density has the potential for being affected by many influences. One of these is the ambient temperature variation in addition to liquid temperatures that are typically compensated. If the sun shines on the analyzer during the day and then turns cold and rains, it is possible that the density measurement is affected. Some vendors recommend insulation to prevent this and possibly a sun shield. The accuracy of the density measurement is stated by one vendor not to be "accurate" unless it is calibrated on that specific crude type. This is due to viscosity and other physical liquid variables. Temperature compensation using the actual liquid temperature measurement instead of making the measurement on the outside surface of the pipe can also affect the answer.

8—ON LINE WATER ANALYZER MEASUREMENT UNCERTAINTIES

On line water analyzers must see a representative sample of the actual flowing stream just like the composite sampler probe. This has always been a requirement for any analysis for water content, density or sampling system. The analyzer will be only as good as the representative sample that is presented to the measurement section.

There has been a lot of information improperly presented in the past as to how "wet oil density" versus "dry oil density" affects analyzers. As the water increases so does the density. The density correction for the baseline zero water content for typical permittivity based analyzers is approximately 0.03% change in water for a 1 $kg/m^3$ change in density. Therefore, for a 10 $kg/m^3$ change in density the change is 0.3% water. A summary of the impact is shown in Table 6. These results are with the oil density set at 860 $kg/m^3$ (approximately 32 API degree) and the water is a 3% salt content which give a water density of 1020 $kg/m^3$.

TABLE 5

On line Water Analyzer Uncertainty Table

| Systematic Uncertainty | Random Uncertainty |
|---|---|
| Density Input Wrong | Ambient Temperature Issues? |
| Liquid Temperature Correction | Data Collection/Software Issues |
| Mixing Not Sufficient | Not Flow Proportional Batch Signal Wrong |
| Low Flow Rate Improper Location High Water Exceeding Range Installation Issues | Reset Wrong |
| At Elbow, On Top or Bottom Crude Oil Properties | |
| Viscosity/Density/Emulsion Calibration Improper | |

TABLE 6

Wet Density Effect on Water Analyzer

Density Oil 860
Density Water 1020 3% Salt Water

| Absolute Water Percent | "Wet" density | Microwave Analyzer Offset Due To Density Oil + Water | Net Reading (%) | Wet/Dry Density Error (%) |
|---|---|---|---|---|
| 0 | 860.00 | 0.000 | 0.00 | 0.00 |
| 1 | 861.50 | −0.046 | 0.95 | 0.05 |

TABLE 6-continued

Wet Density Effect on Water Analyzer

| 2 | 863.00 | −0.092 | 1.91 | 0.09 |
| 3 | 864.50 | −0.137 | 2.86 | 0.14 |
| 4 | 866.00 | −0.183 | 3.82 | 0.18 |
| 5 | 867.50 | −0.228 | 4.77 | 0.23 |
| 8 | 872.00 | −0.363 | 7.64 | 0.36 |
| 10 | 875.00 | −0.452 | 9.55 | 0.45 |
| 12 | 878.00 | −0.540 | 11.46 | 0.54 |
| 15 | 882.50 | −0.671 | 14.33 | 0.67 |
| 20 | 890.00 | −0.887 | 19.11 | 0.89 |
| 30 | 905.00 | −1.309 | 28.69 | 1.31 |
| 40 | 920.00 | −1.717 | 38.28 | 1.72 |
| 50 | 935.00 | −2.111 | 47.89 | 2.11 |

The solution is to hold the earlier density within the analyzer memory for excursions above say 5% water. Then the impact of the density is limited to a very small number as shown in Table 7.

TABLE 7

Hold Density Constant Over 5% Water Measured

Density Oil 860
Density Water 1020

| Absolute Water Percent | "Wet" density | Microwave Analyzer Offset Due To Density Oil + Water | Net Reading (%) | Wet/Dry Density Error (%) |
|---|---|---|---|---|
| 0 | 860.00 | 0.00 | 0.00 | 0.00 |
| 1 | 861.50 | −0.05 | 0.95 | 0.05 |
| 2 | 863.00 | −0.09 | 1.91 | 0.09 |
| 3 | 864.50 | −0.14 | 2.86 | 0.14 |
| 4 | 866.00 | −0.18 | 3.82 | 0.18 |
| 5 | 867.50 | −0.23 | 4.77 | 0.23 |
| 8 | 872.00 | −0.23 | 7.77 | 0.23 |
| 10 | 875.00 | −0.23 | 9.77 | 0.23 |
| 12 | 878.00 | −0.23 | 11.77 | 0.23 |
| 15 | 882.50 | −0.23 | 14.77 | 0.23 |
| 20 | 890.00 | −0.23 | 19.77 | 0.23 |
| 30 | 905.00 | −0.23 | 29.77 | 0.23 |
| 40 | 920.00 | −0.23 | 39.77 | 0.23 |
| 50 | 935.00 | −0.23 | 49.77 | 0.23 |

9—METHOD COMPARISON FOR WATER MEASUREMENT

If no adjustment is made for the "dry oil density" then the data in Table 6 is close to being the error in water percentage for the on line analyzer for those given densities. Now a comparison between the sensitivities using a microwave water measurement which is based on the polar moment of the molecule (the permittivity or at lower frequencies and water percentages, the dielectric constant) and the

TABLE 8

Water Percentage Measurement by MW Analyzer & Density

| MW Water Analyzer | Densitometer & Water % |
|---|---|
| 2,000,000 Hertz Change in Frequency for a 1% Change in Water | If Water has 3% Salt Then Density of Water is 1,030 $kg/m^3$ and Oil Density is 860 $kg/m^3$ then: |
| Analyzer Primarily Sees Water 1%/2,000,000 Hz | 0–100% Water is a change of 170 $kg/m^3$ |

TABLE 8-continued

Water Percentage Measurement by MW Analyzer & Density

| MW Water Analyzer | Densitometer & Water % |
|---|---|
| Approximately 0.03% Change in Water for a 1 kg/m$^3$ change in Density | 1% change in Water is 1.7 kg/m$^3$ If Water has 3% Salt and Oil Density is 960 kg/m$^3$ then: |
| 0.03%/1 kg/m$^3$ Generally 33 Times Less Sensitive to Density Changes Than Using | 0-100% Water is a change of 170 kg/m$^3$ 1% change in Water is 0.7 kg/m$^3$ Density Highly Dependent upon Water |
| Density for Water Measurement | Median 1%/1 kg/m$^3$ | calculation of water percent using density is made in Table 8. The microwave method is more sensitive to the water molecule because the parameter of measurement is the large difference between the small polar moment of crude oils (2.5) and the high polar moment of water (80). With this additional sensitivity the microwave method's ability to resolve water is approximately 33 times greater than that when density is used for measurement.

10—THE OPPORTUNITY TO IMPROVE OVERSIGHT

The opportunity to use more than one independent measurement provides the ability to make a more educated choice as to what method may be less uncertain. Such an opportunity exists using a composite sampler and an on line water analyzer although the sampler results will be considered the correct answer by default. If an additional method was available then there exists an opportunity to better decide which may be the correct answer. The differences between the microwave and density determination of water were given in the previous section. Although these are not totally independent measurements they are sufficient to study as a course of action to better a measurement.

The first issue when using density for water percentage measurement is to determine the dry oil and the produced water density at flowing conditions. If this information can be determined, then the densitometer used for pipeline measurements becomes another check on the final answer to the question "what was the water in the pipeline." The answer lies in the fact that the water analyzer is capable of accuracy at higher water percentages with reduced sensitivity to density. The higher the water percentage the smaller a change in density from the on line density when the low water density is used as in Table 7. The key to this method is to store all of the data for a batch process such as that for ship unloading, well testing or the like and then process the data at the end of the unloading or testing period. In addition, the ability to store the data and then sort it versus some variable such as density, water percentage or flow rate is of interest in the ease of processing the data.

11—SORTING AND ANALYZING THE DATA

Figure 4:
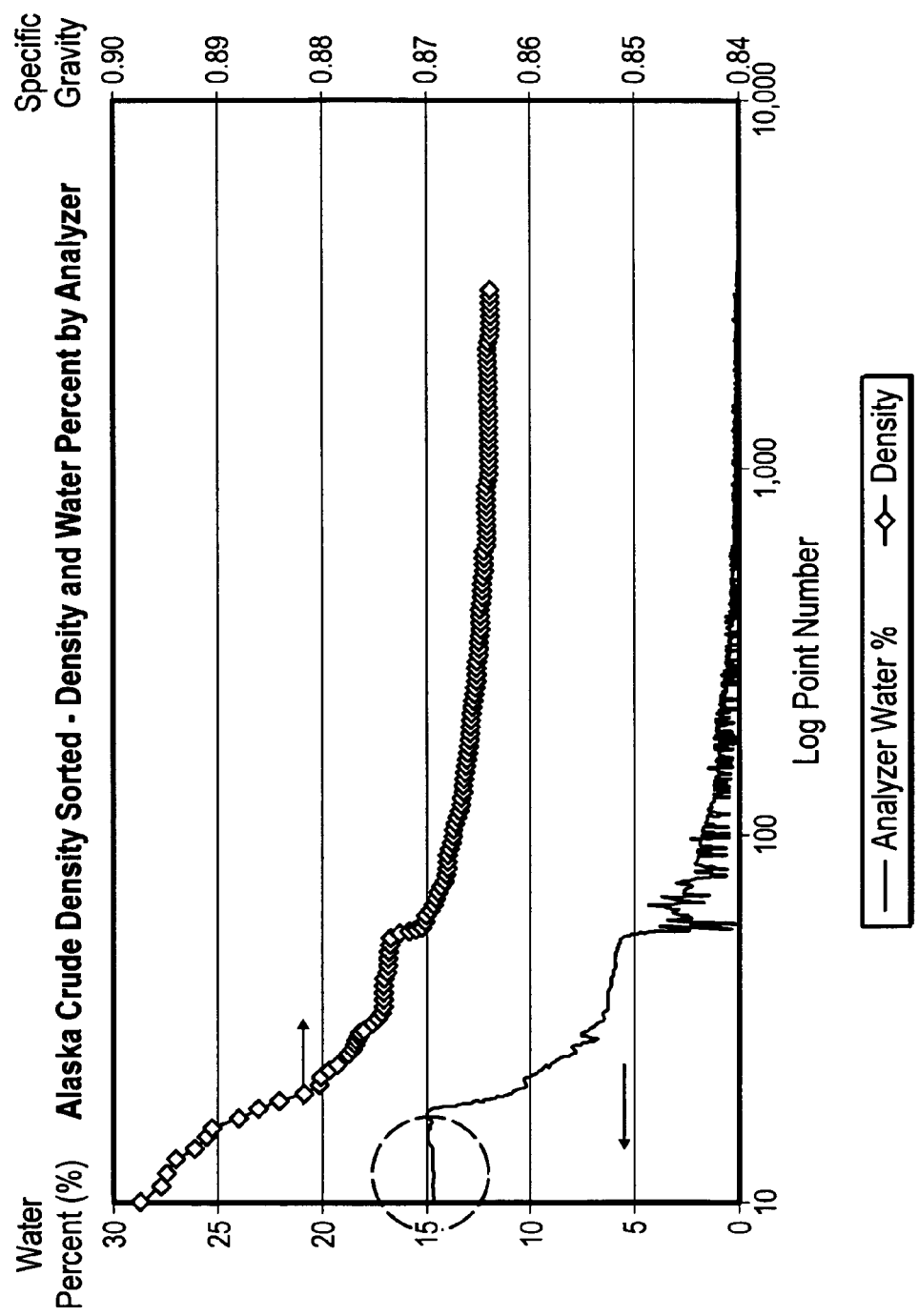
FIGS. 4 and 6 show a re-sorted plots of the data from FIGS. 2 and 3 respectively.

FIG. 4 is the data from the first tanker shown in FIG. 2 with the no flow rate cases removed and then the remaining data sorted by density.

Figure 5:
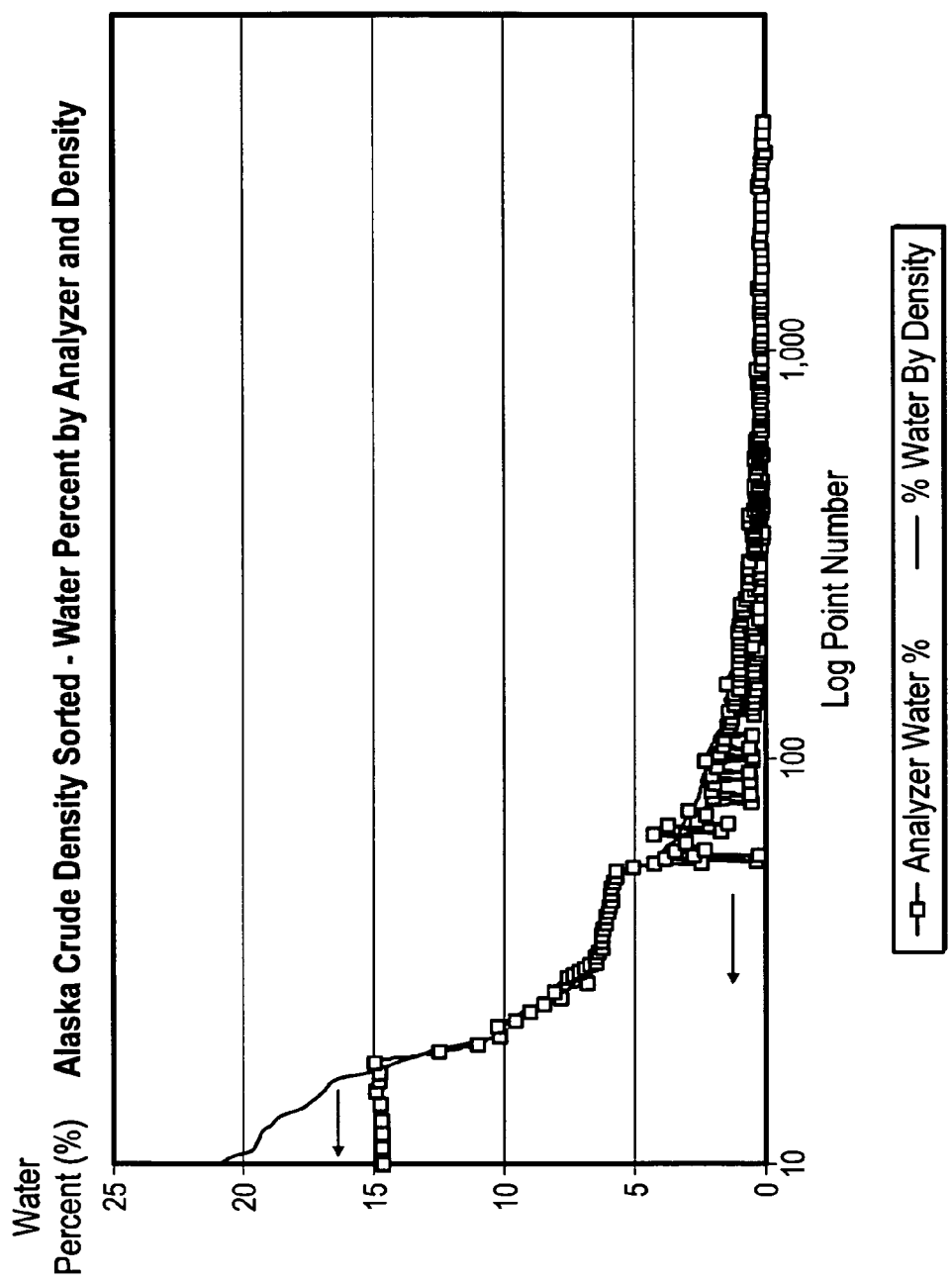
FIG. 5 shows a further transformation of the FIG. 4 data, with data extrema used to calibrate the measurements.

The circled region is where the water percentage exceeded the range of the analyzer and therefore it demonstrates how high the water can be at times. The region starting at 15% water cut and declining is selected to begin the analysis and the minimum specific gravity is used which corresponds to the minimum water percentage. In a simple iterative process a water percentage by density can be calculated to match with to the microwave analyzer's initial high water data points. The result of this analysis provides the following graph of FIG. 5. The resulting density of the oil was 0.864 versus the laboratory of 0.867 and the water density was 1.025. There was no lab density of the water available but, this is close to the expected density from that region. The resulting conclusion is the three methods gave similar results.

12—ANOTHER EXAMPLE

Figure 6:
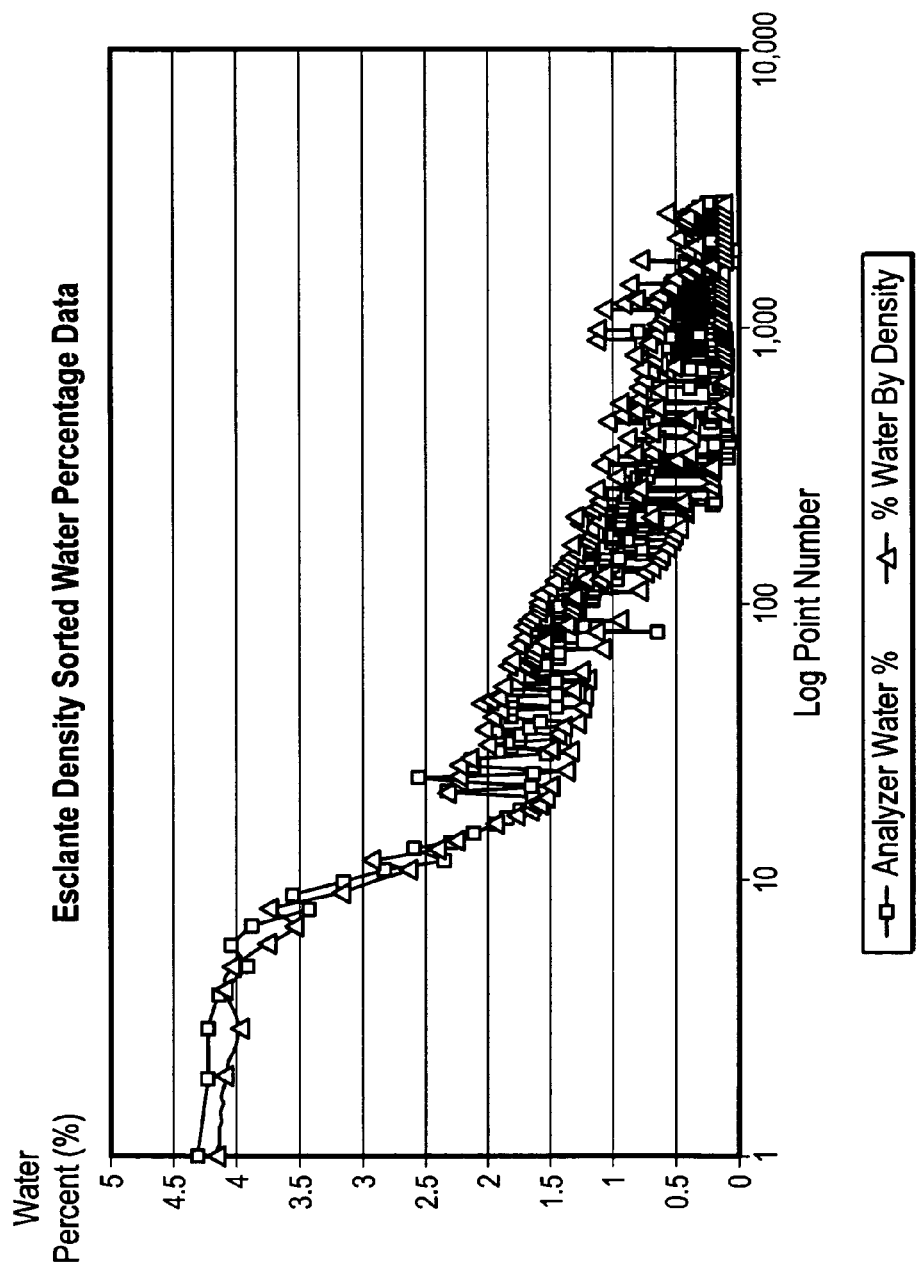

An example with a heavy crude taken from FIG. 3 and sorted for density is shown in FIG. 6. In this example the laboratory was at 0.75% water while the online analyzer average was 0.21%. Notice that the data is based on the log of the data point number so that the beginning fit to the water calculated by density is obvious. It appears visually that the analyzer would have a resulting average well below the laboratory.

This figure appears to demonstrate data for the density that contains much more noise than the data from the Alaskan crude oil data above. A look at the temperature during the discharge was a next step of analysis since the density is temperature corrected.

Figure 7:
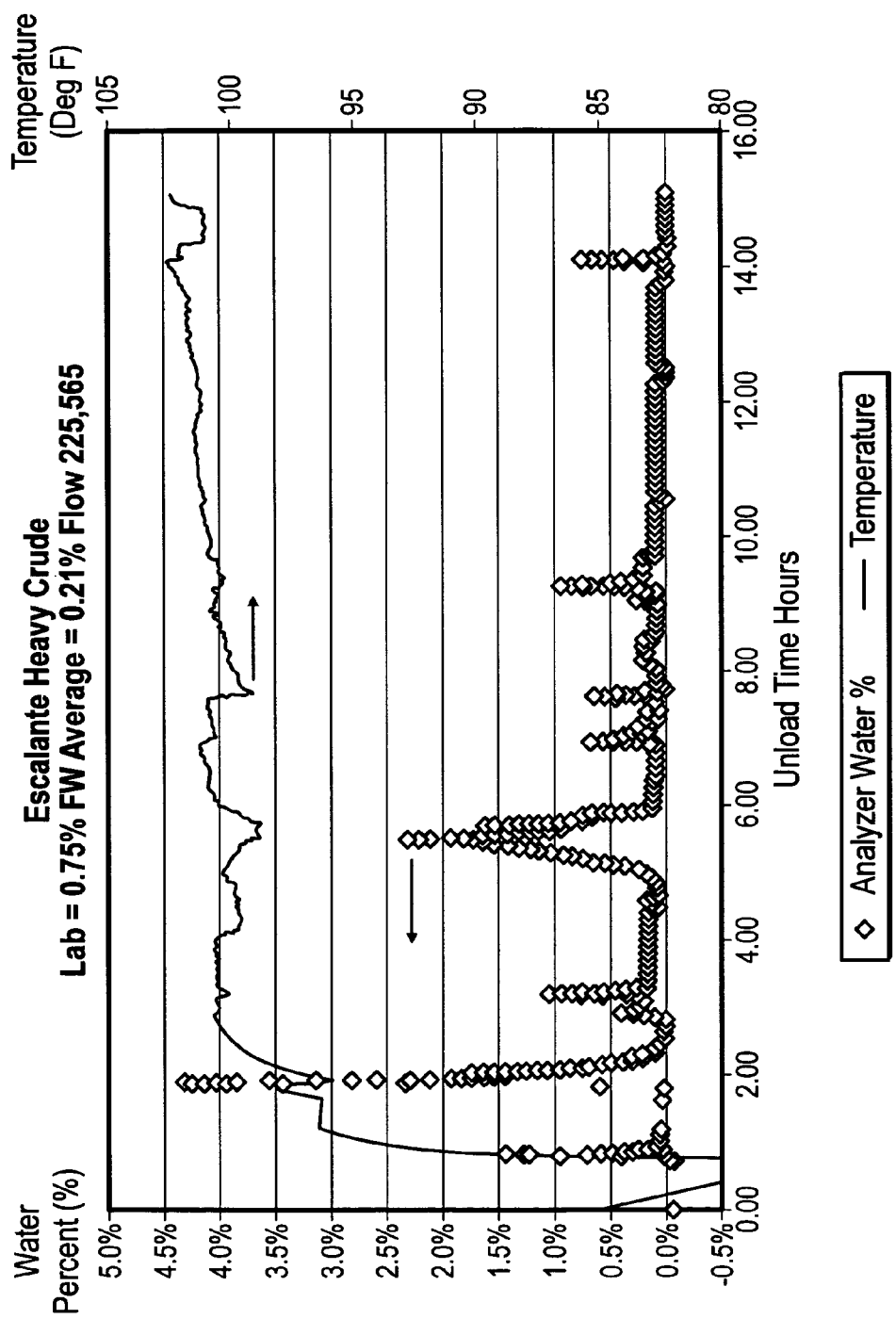
FIG. 7 shows how temperature and water fraction were observed to vary over time.

FIG. 7 shows the temperature and water percentage with time on unsorted data. At several major points where the water was higher the temperature is lower which suggests that the water did not come along with the crude. Theoretically the temperature should be the same or a higher temperature due to the thermal capacity of water being so much higher than the crude oil.

Figure 8:
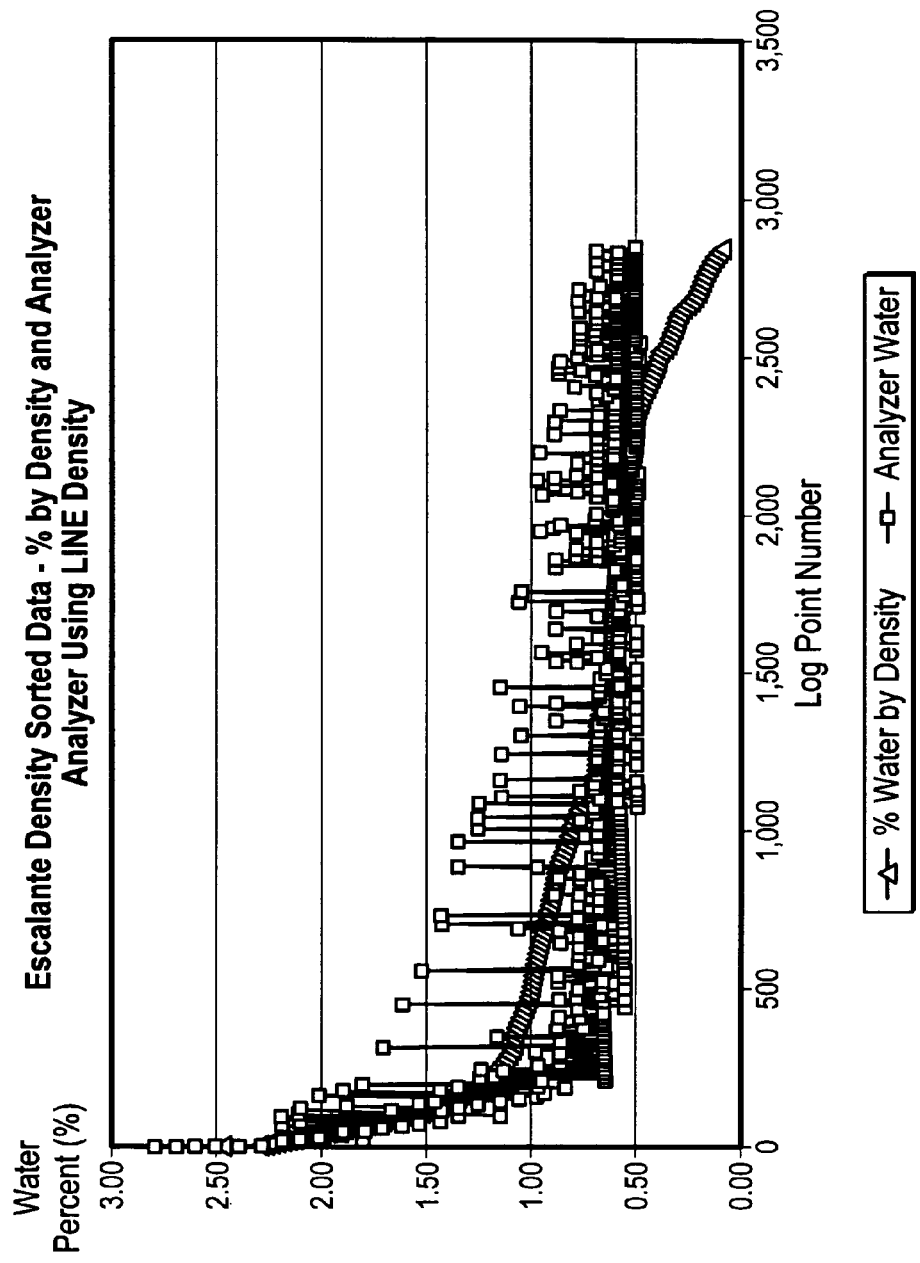
FIG. 8 shows a data curve in which temperature correction was not applied to the analyzer data.
Figure 9:
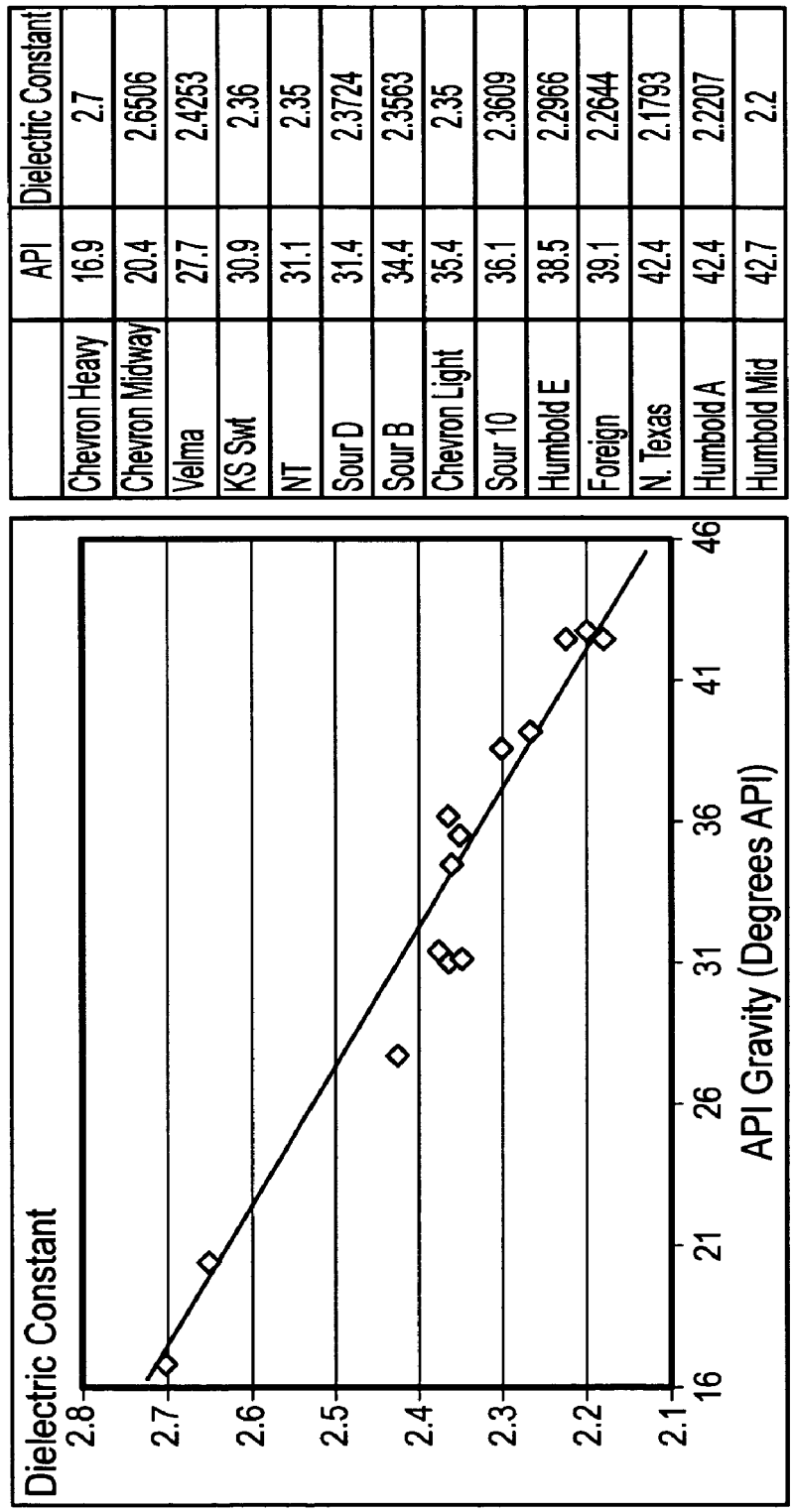
FIG. 9 shows how the dielectric constant of various petroleum products varies as a function of API gravity.

From the observation with temperature the water analyzer was reset to use the line density without any temperature correction. This was not suggesting this is the right answer but instead to compare the results and curve shapes. FIG. 8 shows the resulting water by analyzer that levels off to a reasonably consistent number.

13—CONCLUSION

Although the composite sampler will be around for many more years, the on line real time companion may aid in improving the measurement. In addition, data techniques may allow an independent set of measurements by which validation of the results can be compared. When differences occur, they can be identified and resolved if the data obtained during routine operation can determine that a question should be asked. The data obtained from composite samplers is not real time and can only provide answers that are obtained by human involvement after the batch has left the station. Analytical measurement coupled with the computing power that is now available will change the way pipeline data on water cut is collected and analyzed. Methods to prove the viability of this approach are just now being tested. Among the remaining things to be understood and defined are how to automatically process the data and alert an operator that some further inspection of the data or comparisons are required.

With the current price of petroleum products exceeding US $50 per barrel, methods to measure and validate the transfer of crude oil must be improved. Real time on line analyzers should become a valuable tool in this pursuit of a better measurement. If the real example in FIG. 3 was used where the difference of 0.54% in water delivered between the composite sampler (0.75% water) and the on line analyzer (0.21%) across 225,565 barrels would be a difference of US $60,903.

For contrast with Table 2, Table 9 (below) shows how the analyzer error would accumulate significantly if no water content set point is used to cut off such accumulation. Instead, the offset values for the entire set of water content measurements are corrected based on their corresponding wet density measurements. The error increases up to 2.11% at an absolute water content of 50%. The use of the water content set point allows the dry oil density to be estimated using the wet density measurements at low water content, thereby preventing the error from becoming too large.

TABLE 9

Wet Density Effect on Water Analyzer

| Density Oil | 860 kg/m^3 |
| Density Water | 1020 kg/m^3 |

| Absolute Water Percent | "Wet" density | Microwave Analyzer Offset Due To Density Oil + Water | Net Reading (%) | Wet/Dry Density Error (%) |
|---|---|---|---|---|
| 0 | 860.00 | 0.000 | 0.00 | 0.00 |
| 1 | 861.50 | −0.046 | 0.95 | 0.05 |
| 2 | 863.00 | −0.092 | 1.91 | 0.09 |
| 3 | 864.50 | −0.137 | 2.86 | 0.14 |
| 4 | 866.00 | −0.183 | 3.82 | 0.18 |
| 5 | 867.50 | −0.228 | 4.77 | 0.23 |
| 8 | 872.00 | −0.363 | 7.64 | 0.36 |
| 10 | 875.00 | −0.452 | 9.55 | 0.45 |
| 12 | 878.00 | −0.540 | 11.46 | 0.54 |
| 15 | 882.50 | −0.671 | 14.33 | 0.67 |
| 20 | 890.00 | −0.887 | 19.11 | 0.89 |
| 30 | 905.00 | −1.309 | 28.69 | 1.31 |
| 40 | 920.00 | −1.717 | 38.28 | 1.72 |
| 50 | 935.00 | −2.111 | 47.89 | 2.11 |

Table 2 above shows how error is reduced by using the disclosed inventions. This table's offset values assume that the water content set point is about 5%. This water content percentage may be weight %, volume %, or mole % depending on the type of readings taken by the on-line analyzer. In this case, the calibration density of the on-line analyzer is assumed to be 860 kg/m³, and the slope correction factor is assumed to be 0.03%.

As shown in Table 2 above, the wet density measurements corresponding to those water content measurements less than or equal to 5% are employed to determine the offset values. On the other hand, the offset values for the water content measurements greater than 5% are determined based on the wet density measurement corresponding to the 5% water content measurement, i.e., the water content set point. As such, the analyzer error only increases up to 0.23%.

In various embodiments, methods of correcting on-line analyzer measurements of the content of a first component in a multiple-component fluid, comprise: correcting first component content measurements taken using an on-line analyzer based on an offset value calculated for each first component content measurement using the following equations:

if the first component content measurement is ≦ a predetermined content set point, offset=slope correction factor×(a corresponding mixture density measurement−calibration density); and  (a)

if the first component content measurement is > the predetermined content set point, offset=the offset value calculated at the predetermined content set point.  (b)

It has been discovered that the water content measurements taken by an on-line analyzer of flowing petroleum may be corrected using wet density measurements taken by an on-line densitometer by adding offset values to the water content measurements. An offset value for a particular water content measurement may be calculated using the following equations:

if the water content measurement is ≦ a water content set point, offset=slope correction factor×(a corresponding wet density measurement−calibration density); and  (a)

if the water content measurement is > the water content set point, offset=the offset value calculated at the water content set point.  (b)

The slope correction factor is the change in the water content measurement per unit change in the wet density of the petroleum relative to the calibration density, where the calibration density may be the density of the dry oil during the calibration of the on-line analyzer. Thus, through the use of the slope correction factor, the offset value attempts to account for the error in the water content measurement due to the change in wet oil density. For each degree change in API gravity, there may be a change of about 0.01 in dielectric constant, which represents about 0.5% change in dielectric constant depending on the dielectric constant of the particular crude oil. Thus, the slope correction factor for the baseline zero water content of permittivity-based analyzers is usually about 0.16% change in water per 1° API change in density or 0.03%/kg/m³. See George Kite, *Commingling and Well-Testing Operations*, J. Petroleum Tech. 732-733 (March 1964), which is incorporated by reference herein in its entirety. However, the slope correction factor could be different depending on whether the petroleum includes relatively high or low density components.

The offset value, also known as the calibration factor, may further account for the error in the water content measurement due to the change in the dry oil density. This error is only allowed to increase up to a maximum water content set point at which the error is then maintained at the same value. In this manner, the wet density measurements taken when the water content is relatively low may be used to estimate the dry oil density, which is unknown. Otherwise, the error would undesirably accumulate significantly above the set point as described in more detail later.

On-line analyzer measurements of the content of a first component in a multiple-component fluid may be corrected using corresponding mixture density measurements of the fluid using a densitometer. The on-line analyzer is defined herein as a permittivity-based analyzer such as a microwave analyzer, a capacitance analyzer, a RF analyzer, or combinations thereof. Further, the densitometer may be an on-line densitometer such as a coriolis, a vibrating fork densitometer, a speed of sound densitometer, or combinations thereof. The offset value for each first component content measurement may then be determined in accordance with the following equations:

if the first component content measurement is ≦ a predetermined content set point, offset=slope correction factor×(the corresponding mixture density measurement−a calibration density); and  (a)

if the first component content measurement is > the predetermined content set point, offset=the offset value calculated at the predetermined content set point.  (b)

The offset value represents the error in first component content measurement due to the change in density of the second component. The slope correction factor is defined as the change in the first component content measurement per unit change in the mixture density relative to the calibration density. In an embodiment in which the fluid being analyzed is petroleum, the calibration density represents the density of the dry oil during the calibration of the on-line analyzer.

Based on the calculated offset values, the first component content measurements obtained using an on-line analyzer may be corrected in accordance with the following equation:

final first component content=measured first component content+offset value.

In one embodiment, the multiple-component fluid may be petroleum produced by a subterranean formation. The petroleum may contain gas, water, and/or oil. As such, an on-line analyzer may be employed to detect the amount of water in the petroleum as it flows in a pipeline out of a well or to a refinery or as it flows into or out of a tank for holding the petroleum as it is transported on land or on water via a ship. The water content measurements (i.e., the first component content measurements) taken by the on-line analyzer may be corrected for wet density and dry density in the manner described above using the wet density measurements (i.e., the mixture density measurements) taken by a densitometer.

In further embodiments, methods of correcting on-line analyzer measurements of the content of a first component in a multiple-component fluid, comprise: taking first component content measurements in a flowing multiple-component fluid using an on-line analyzer; taking mixture density measurements that correspond to the first component content measurements using a densitometer; calculating an offset value for each first component content measurement based on the following equations:

if the first component content measurement is ≦ a predetermined content set point, offset=slope correction factor×(the corresponding mixture density measurement−a calibration density); and  (a)

if the first component content measurement is > the predetermined content set point, offset=the offset value calculated at the predetermined content set point; and  (b)

correcting the first component content measurements based on the respective offset values.

In additional embodiments, methods of correcting on-line analyzer measurements of water content in a multiple-component fluid, comprise: taking water content measurements in a multiple-component fluid using an on-line water analyzer as the fluid flows through a pipeline or into or out of a tank; taking wet density measurements that correspond to the water content measurements using a densitometer; calculating an offset value for each water content measurement based on the following equations:

if the water content measurement is ≦ a predetermined water content set point, offset=a slope correction factor×(the corresponding wet density measurement−a calibration density); and  (a)

if the water content measurement is > the predetermined water content set point, offset=the offset value calculated at the predetermined water content set point; and  (b)

correcting the water content measurements based on the respective offset values.

Modifications and Variations

As will be recognized by those skilled in the art, the innovative concepts described in the present application can be modified and varied over a tremendous range of applications, and accordingly the scope of patented subject matter is not limited by any of the specific exemplary teachings given.

For example, a variety of analyzer configurations can be used, as described in the numerous patents and published applications of Phase Dynamics Inc.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method of correcting on-line analyzer measurements of the content of a first component in a multiple-component fluid, comprising:

correcting first component content measurements taken using an on-line analyzer based on an offset value calculated for each first component content measurement using the following equations:

if the first component content measurement is ≦ a predetermined content set point, offset=slope correction factor×(a corresponding mixture density measurement−calibration density); and  (a)

if the first component content measurement is > the predetermined content set point, offset=the offset value calculated at the predetermined content set point  (b).

2. The method of claim 1, wherein the on-line analyzer comprises a capacitance analyzer, a RF analyzer, a microwave analyzer, or combinations thereof.

3. The method of claim 1, wherein the slope correction factor is $0.03\%/\text{kg/m}^3$.

4. The method of claim 1, wherein the slope correction factor is $0.16\%/°\text{ API}$.

5. The method of claim 1, wherein the corresponding first component density measurements are taken using an on-line densitometer.

6. The method of claim 1, wherein the first component is water, and a second component in the multiple-component fluid is oil.

7. The method of claim 6, wherein the predetermined content set point is 5% water.

8. A method of correcting on-line analyzer measurements of the content of a first component in a multiple-component fluid, comprising:

taking first component content measurements in a flowing multiple-component fluid using an on-line analyzer;

taking mixture density measurements that correspond to the first component content measurements using a densitometer;

calculating an offset value for each first component content measurement based on the following equations:

if the first component content measurement is ≦ a predetermined content set point, offset=slope correction factor×(the corresponding mixture density measurement−a calibration density); and  (a)

if the first component content measurement is > the predetermined content set point, offset=the offset value calculated at the predetermined content set point; and  (b)

correcting the first component content measurements based on the respective offset values.

9. The method of claim 8, wherein the on-line analyzer comprises a capacitance analyzer, a RF analyzer, a microwave analyzer, or combinations thereof.

10. The method of claim 8, wherein the slope correction factor is $0.03\%/\text{kg/m}^3$.

11. The method of claim 8, wherein the slope correction factor is $0.160\%/°\text{ API}$.

12. The method of claim 8, wherein the densitometer comprises an on-line densitometer.

13. The method of claim 8, wherein the first component is water, and a second component in the multiple-component fluid is oil.

14. The method of claim 13, wherein the predetermined content set point is 5% water.

15. A method of correcting on-line analyzer measurements of water content in a multiple-component fluid, comprising:
   taking water content measurements in a multiple-component fluid using an on-line water analyzer as the fluid flows through a pipeline or into or out of a tank;
   taking wet density measurements that correspond to the water content measurements using a densitometer;
   calculating an offset value for each water content measurement based on the following equations:

if the water content measurement is $\leq$ a predetermined water content set point, offset=a slope correction factor×(the corresponding wet density measurement−a calibration density); and (a)

if the water content measurement is > the predetermined water content set point, offset=the offset value calculated at the predetermined water content set point; and (b)

correcting the water content measurements based on the respective offset values.

16. The method of claim 15, wherein the on-line analyzer comprises a capacitance analyzer, a RF analyzer, a microwave analyzer, or combinations thereof.

17. The method of claim 15, wherein the multiple-component fluid comprises water and oil.

18. The method of claim 15, wherein the predetermined water content set point is 5%.

19. The method of claim 15, wherein the slope correction factor is 0.03%/kg/m$^3$.

20. The method of claim 15, wherein the slope correction factor is 0.16%/° API.

* * * * *